(12) United States Patent
Loewy et al.

(10) Patent No.: US 6,326,149 B1
(45) Date of Patent: Dec. 4, 2001

(54) METHOD FOR CONTROLLED ELECTROSTATIC ADHERENT DEPOSITION OF PARTICLES ON A SUBSTRATE

(75) Inventors: Zyi Gerald Loewy, Fair Lawn; William Chiang, Monmouth Junction; Hoi Cheong Sun, Dayton; Bryan Lloyd Bentz, Princeton, all of NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 09/432,745

(22) Filed: Nov. 2, 1999

Related U.S. Application Data

(60) Provisional application No. 60/106,817, filed on Nov. 3, 1998.

(51) Int. Cl.[7] .............................. C12Q 1/68; B05D 1/04; B05D 1/12; H05C 1/00
(52) U.S. Cl. ................. 435/6; 427/458; 427/180
(58) Field of Search .......................................... 435/6, 136

(56) References Cited

U.S. PATENT DOCUMENTS

| | | | |
|---|---|---|---|
| 4,868,105 | 9/1989 | Urdea et al. .............. 435/6 |
| 5,200,270 | 4/1993 | Ishida et al. .............. 428/403 |
| 5,391,272 | * 2/1995 | O'Daly et al. .............. 204/153.12 |
| 5,424,188 | 6/1995 | Schneider et al. .............. 435/6 |
| 5,595,893 | * 1/1997 | Pometto, III et al. .............. 435/136 |
| 5,741,662 | 4/1998 | Madsen et al. .............. 435/34 |
| 5,770,370 | * 6/1998 | Kumar .............. 435/6 |
| 6,004,752 | * 12/1999 | Loewy et al. .............. 435/6 |
| 6,051,380 | * 4/2000 | Sosnowski et al. .............. 435/6 |

\* cited by examiner

Primary Examiner—Kenneth R. Horlick
Assistant Examiner—Teresa Strzelecka
(74) Attorney, Agent, or Firm—William J. Burke

(57) ABSTRACT

Provided is a method of fabricating a substrate having on a surface thereof two or more spatially-resolved regions, each with a defined amount or concentration of one of one or more chemical components, the method comprising: associating a chemical component with particles of 1 $\mu$m to 500 $\mu$m diameter; electrostatically depositing the particles on the appropriate regions; and if a said spatially-resolved region is to receive a second chemical component, repeating steps (a) and (b) for that chemical component and the appropriate regions.

20 Claims, 1 Drawing Sheet

METHOD FOR CONTROLLED ELECTROSTATIC ADHERENT DEPOSITION OF PARTICLES ON A SUBSTRATE

This application claims priority of provisional patent applications to Loewy, et al. Ser. No. 60/106,817, filed Nov. 3, 1998.

The present invention relates to methods of fabricating surfaces on which defined amounts of chemical components are present in spatially resolved segments, and to substrates fabricated with such defined, resolved segments on their surface.

The present invention pertains to improved fabrication methods and technology tools to increase the availability and diversity of low cost, point of care/home health testing kits. Such methods and technology tools include the dry deposition of charged reagents and powders, preferably medicaments, on a variety of surfaces for applications in the pharmaceutical industry and health care industry. These dry reagent deposition methods and tools can provide high speed, low cost manufacturing and thus are well suited to develop products for the home health testing industry, particularly for use in populations with limited access to low cost health care. Such products are user-friendly, non-mechanical, stable, accurate, precise, sensitive, specific and quantitative. The methods of the present invention are appropriate for using electrostatics to deposit biomolecule reagent microparticles on a membrane for a point of care/home health testing assay.

An important element of the present invention is the recognition that the amounts of biomolecules or the like that need to be associated with a substrate for useful diagnostic tools are often less than the amounts typically directly deposited by electrostatic deposition. These biomolecules can be associated with particles in an appropriate amount, and the particles are usefully employed in electrostatic depositions to economically and reliably fabricate test strips. Appropriate use of the deposition engine allows spatially resolved depositions of biomolecules, for instance to create reagents that develop visual indications such as "+" or "−" signs. Unexpectedly, the carrier particles and compositions used to retain the carrier particles do not interfere with bioassays.

SUMMARY OF THE INVENTION

The invention provides a method of fabricating a substrate having on a surface thereof two or more spatially-resolved regions, each with a defined amount or concentration of one of one or more chemical components, the method comprising: associating a chemical component with particles of 1 $\mu$m to 500 $\mu$m diameter; electrostatically depositing the particles on the appropriate regions; and if a said spatially-resolved region is to receive a second chemical component, repeating steps (a) and (b) for that chemical component and the appropriate regions. Preferably, the chemical component comprises 20% w/w or less (more preferably 10% w/w or less, or 5% w/w or less) of the particles In one embodiment, the chemical component is associated with preliminary particles, and the first particles are aggregated with other solid components to form the particles of 1 $\mu$m to 500 $\mu$m diameter. In certain embodiments, the chemical component is bioactive agent, a peptide, a protein, a nucleic acid, a nucleic acid-intercalating dye. The associating can, for example, comprise covalently attaching or associating with an association constant of at least $10^{12}$ $M^{-1}$. Preferably, the method further includes coating the regions with a polymer composition adapted to secure the particles to the surface.

The invention includes substrates produced by the method.

The invention further includes a method of fabricating a cell growth supporting substrate with spatially-resolved regions with associated bioactive agents comprising associating the bioactive agents with the cell growth supporting substrate or a separate substrate that is incorporated into the cell growth supporting substrate with the method. The bioactive agent can be, for example a nutrient or an antimicrobial agent.

The invention further includes a substrate comprising: a first layer comprising a chemical component supporting an assay reaction, the layer formed by the method; and a second layer comprising a second chemical component, distinct from the first, supporting the assay reaction. The substrate can comprise a reagent that facilitates visualization of a reaction product, such as colloidal gold or horse radish peroxidase.

BRIEF DESCRIPTION OF THE DRAWINGS

FIG. 1A shows a two layer deposition;

FIG. 1B shows a deposition using a mixture of applied components; and

FIG. 1C shows depositions conducted with an intervening polymer coating.

DETAILED DESCRIPTION OF THE INVENTION

Molecular diagnostic assays utilize or incorporate biomolecules of some type in their design. The biomolecules include species such as nucleic acids, proteins, peptides, enzymes can be used in the present invention. For example, U.S. Pat. No. 5,939,261 discloses a method for capturing nucleic acid molecules on a substrate, which method can be used with the present invention. The methods of the invention are applicable to depositing a variety of biological macromolecules, for example, for purposes of creating diagnostics and assays.

Particle/Chemical Component Association

The present invention provides for associating a chemical component with particles and electrostatically depositing the particles on a substrate. The particles can be selected to be of a particular size range and of a material selected to provide association of one or more chosen chemical components. For example, the particle range can be 1 $\mu$m to 500 $\mu$m in diameter, preferably, 50 $\mu$m to 400 $\mu$m, more preferably 150 $\mu$m to 250 $\mu$m. The methods of the invention also include the association of chemical components with preliminary particles smaller than the particles described above and the formation of aggregates between preliminary particles and other particles which can be with or without an associated chemical component. The preliminary particles are preferably polymeric particles that resist fragmentation when manipulated, such as a fluidized bed or the like. Among preferred particles are latex particles. Preferably, such particles are 0.1 $\mu$m to 5 $\mu$m in diameter, more preferably 0.1 $\mu$m to 1 $\mu$m.

The chemical component(s) can include biological macromolecules of interest, or fragments thereof, a bioactive agent, a protein, or a nucleic acid. The chemical component (s) can also be compounds of selective permeability, components of varying hydrophobicity, porosity, packing density, reactivities, or other varying chemical/physical properties. Chemical components can be applied in submonolayer, monolayer or multilayer levels on the substrate particles. Multilayer level application of chemical components on substrate particles (or beads) can include coating the substrate with an observable quantity of the chemical component. The chemical component(s) can also be a bioactive agent that is a nutrient or an antimicrobial agent.

The invention provides conditions sufficient for association of the particle and one or more chemical components thereto. The particle material, chemical component identity, any reaction conditions or other parameters can be selected to achieve covalent attachment or association of one or more of the chemical component with an association constant, preferably of at least $10^{12}$ or $10^{15}M^{-1}$. Association of the chemical component with the particles may comprise multiple reaction steps, including the physical and chemical modification of the particle, in whole or in part, or of the chemical component. Covalent associations include couplings mediated by carbodiimides or like dehydrating agents, as outlined for example in *Biomagnetic Techniques and Molecular Biology*, $2^{nd}$ Edition, Dynal, Oslo, Norway.

The methods of the invention can include mixing the particles with an inert carrier. This carrier can be a powder, for example a sugar. In some embodiments of the invention, particles with a chemical component associated thereto are mixed with a sugar to avoid difficulties of preparing and handling small amounts of dry chemical components directly. In some embodiments, the particle size can be measured before or after the particles are mixed with a carrier. Particle size reduction of the mixture or the substrate particles may be performed to achieve a desired range of particle sizes, for example by sieving the powder or powder mixture through a mesh screen.

The substrates make according to the invention can be adapted for use in chemical processes that are monitored with an apparatus, such as a spectrophotometric apparatus, or visually.

Electrostatic and Controlled Field Deposition

Figure 1:
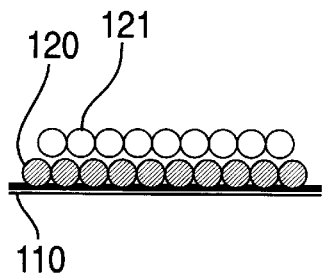
FIG. 1 displays examples of deposition configurations that can be produced by the inventive method. More specifically.
Figure 1:
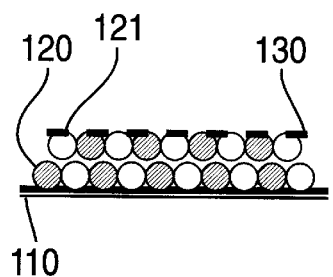
Figure 1:
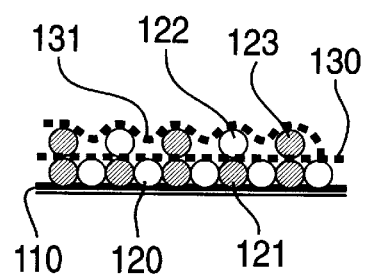

The methods of the invention further comprise electrostatically depositing one or more particle/chemical component associated complexes onto the surface of a substrate so as to form two or more spatially-resolved regions on the surface. Electrostatic deposition can be performed using various appropriate methods and devices known in the art, some of which are discussed below. One skilled in the art would select an electrostatic deposition device and method appropriate for a given application. In some embodiments, the substrate can be a membrane made, for example, a nitrocellulose (Schleicher and Schuell, Keene, N.H.) or acetate membrane. The substrate can be charged or neutral overall, and may have regions of charge aggregation or localized acid or base sites. In one embodiment of the invention, multiple depositions can be used to place particles with different chemical components in spatially-resolved regions of the substrate surface. Multiple chemical components can be associated with a given particle in the methods of the invention. Multiple layers of particles each associated with separate (discrete) chemical components can be provided by the methods of the present invention (FIG. 1). Thus, the invention provides for electrostatically depositing particles having one or more discrete chemical components associated thereto on the surface of a substrate in two or more spatially-resolved regions, in one or more layers or any combination of spatial and layer resolution desired and practicable.

In some electrostatic deposition methods, a substrate is sufficiently electrically isolated so that an electrostatic charge can be accumulated on the substrate. One means of accumulating the charge is by taking advantage of the photoelectric effect. In this method the substrate is exposed to electromagnetic radiation effective to strip charges, typically electrons, from the surface of the substrate. Other methods include induction charging or tribocharging, plasma treatment, induction charging and corona charging. In a more preferred method, an ion emitter is oriented towards the surface on which one intends to create a charge and operated. Such methods of ion printing to controllably electrostatically deposit charged materials such as powders are described in detail in Pletcher et al., U.S. Pat. No. 5,714,007, issued Feb. 3, 1998, U.S. Pat. No. 6,007,630 and U.S. Pat. 6,074,688.

It should be noted that where the average charge-to-mass ratio of the charged particles of the deposition material is known, the mass of particles that will effectively deposit can be relatively accurately predicted from the amount of charge previously accumulated on the substrate. In particular, for a given type of substrate a calibration database can be compiled. For a given average charge-to-mass ratio of the applied particles, the relationship of accumulated charge to deposited mass can be calibrated for a given set of materials and charging conditions. In a production protocol, the average charge-to-mass ratio of the particles can be monitored. The illustrative charge-to-mass monitor functions by applying a voltage to a crystal such as a quartz crystal to establish a vibratory frequency, monitoring changes in the vibratory frequency when exposed to the charged particles, and correlating these changes to the mass of the particles that impact the monitor. Another charge-to-mass monitor uses the cage blowoff method of C. B. Schein and J. Cranch, J. Applied Phys. 46: 5140, 1975. With the use of one or more charge-to-mass monitors, feedback loops can be incorporated into the electrical controls of a deposition apparatus. In one preferred embodiment, a charge-to-mass monitor is positioned to sample the charge-to-mass of particles at their source (examples for source devices described below) and a charge monitor (for example a device for measuring currents created by the deposition of charged particles) is positioned adjacent to the site of deposition. The sampling values produced at these two sites provide diagnostic data on the operation of the deposition apparatus.

A number of additional methods can be used to monitor the amount of material that is deposited on a solid support. For example, optical methods can include measuring reflectance, transmission, or fluorescence using laser or non-collimated light of broad or narrow band width. See, for example, Poliniak et al., "Dry Powder Deposition Apparatus," U.S. Pat. No. 6,063,194. Other sources of directed electromagnetic energy can be used, for instance X-ray absorption or fluorescence or microwave absorption can be used. A tuned circuit can be used to monitor an endpoint at which deposited material creates a resonance with an energy source such as a microwave energy source. Acoustic absorption can also be used, where preferably the sound source is an ultrasound source. Another exemplary measuring method can use a profilameter, which is a laser device that measures the amount the a beam of light is deflected by a surface with deposited material to measure the depth of the deposited material. Further electrical methods can include measuring a capacitance between a conductive material associated with the solid support (for example a conductive material incorporated into the solid support or a conductive material that has the solid support positioned adjacent to it) and another conductor, where the deposited material is located between the two conductors.

A variety of additional factors can be monitored or controlled to increase the reproducibility of the charge-to-mass ratios generated by the charged deposition material source. For example, controlling the humidity of the local environment, the nature and content of bound solvent in the materials sought to be deposited, the purity of materials sought to be deposited, and the rubbing velocity effected in the tribocharging process can be important.

Another method of electrostatically depositing charged deposition materials to a surface has been termed "controlled field deposition," and typically involves applying a potential to an electrode which directly or indirectly results in the formation of an attractive electrical field at the surface upon which charged material will be deposited. For example, a substrate can have electrical conductors positioned below the deposition surfaces, and a potential applied to the conductors results in the formation of an attractive field at the surface. Where the separation between the substrate's surface and the conductors is sufficiently small, once an external potential is no longer applied to the conductors the charge of the deposition material results in a charge redistribution in the conductors such that an electrostatic "image" force is formed between the deposition material and the conductors, thereby helping to stabilize the deposition material's adherence to the surface. It should be noted that for many particles the charge of the particles resists discharge even when deposited directly on a conductor, thereby allowing the image force, which can be very large, to effect the particles over several hours or days.

The field generating devices for controlled field deposition can be designed (a) to directly apply deposition material onto apparatuses that incorporate electrodes for generating the field or (b) for use with electrostatic chucks (i.e., field application structures) which operate in conjunction with the substrate on which deposition material is to be applied. In the former case (a), it is generally desirable that the metallization processes used to create the electrodes is susceptible to mass production techniques. For example, the metallization can be created by lithographic techniques where finely patterned electrodes are sought or by adhering or fusing metal layers to the substrate. In design (b), the electrostatic chuck can be effective to electrostatically adhere the substrate to the chuck, but the use of vacuum to provide or supplement the adherent force can be desirable. A third option is that the substrate is designed to reversibly couple with a device that provides the electrodes, such that the substrate and the coupled device provide a field-generating apparatus. In this way, the electrode structures that can be a source of manufacturing costs remain separate from the consumable on which reagents for conducting a chemical process will be deposited. In addition to the documents recited above, further information on electrode structures and electrostatic chucks can be found in Sun, "Chucks and Methods for Positioning Multiple Objects on a Substrate," U.S. Pat. No. 5,788,814, issued Aug. 4, 1998.

The charge of the particles applied to a substrate can be generated for example by plasma treatment, radiation treatment (including treatment with suitably high energy electromagnetic radiation) or ion bombardment. More preferably, however, the charge is generated by induction tribocharging, wherein two materials with differing triboelectric constants rub against each other and transfer charge between one another. Tribocharging is more preferred over the enumerated charge-producing methods because it exposes the particles to the least amount of reaction-promoting energy, and hence the tribocharging method is less susceptible to causing compounds to degrade. Examples of materials that can be used for tribocharging include polytetrafluoroethylene ("TEFLON"), and polymers of chlorotrifluoroethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K.C. Frisch and A. Patsis, Electrical Properties of Polymers (Technomic Publications, Westport, CT), which article is hereby incorporated by reference in its entirety. For example, polytetrafluoroethylene and polyethylene and other negatively charged materials will generally create a positive charge on an object. Nylon and other positively charged materials will generally create a negative charge on an object. Tribocharging and appliances for dispensing charged particles are describe in Sun et al., "Acoustic Dispenser," U.S. Pat. No. 5,753,302. U.S. Pat. No. 5,753,302 describes, in particular, an acoustic dispenser that uses vibratory energy and gating electric fields to dispense charged particles for deposition onto the substrate, and is incorporated herein by reference in its entirety.

Adhering Deposited Powder to Substrate

Powder deposited on a substrate surface is often very loosely bound at least after the image force dissipates or the conductor creating the image force is removed. If the surface is physically shaken, inverted or otherwise agitated, any powder pattern on the surface can dislodge and the powder can be dispersed.

The method of the present invention provides for adhering loosely bound particles, for instance a powder or powder/carrier mixture, to a surface. The method preferably allows for the surface-deposited powder to be handled or transported without the loss or displacement of the powder. The method of the invention can be used, for example, with charged powders or charged powder/carrier powder mixtures that have been electrostatically deposited onto a substrate surface. The method of powder adherence to a substrate of the invention can be used in conjunction with any particle association and electrostatic deposition methods described above. Preferably, the particles are adhered while an image force acts to preliminarily secure the particles.

In a preferred embodiment, the method of adhering particles to a surface comprises coating regions of the deposited particles with a film-forming polymer. Examples of such polymers are well known in the art. One example is a mixture of polyvinylpyrrolidone (PVP), polyethylene glycol (PEG) and nonionic surfactant, as described an example below. In one embodiment, the polymer can be coated by using a fogging apparatus described in FIG. 2, which produces a gentle fog of material which, after landing on the deposited powder, acts to prevent the removal of the powder from the membrane. This procedure results in the deposited powder being well-bound to the membrane. Polymers, polymer mixtures, and deposition conditions can be selected by one skilled in the art to produce films with desired physical characteristics, such as permeability, thickness, melting point, glass transition temperature, and the like.

Figure 2:
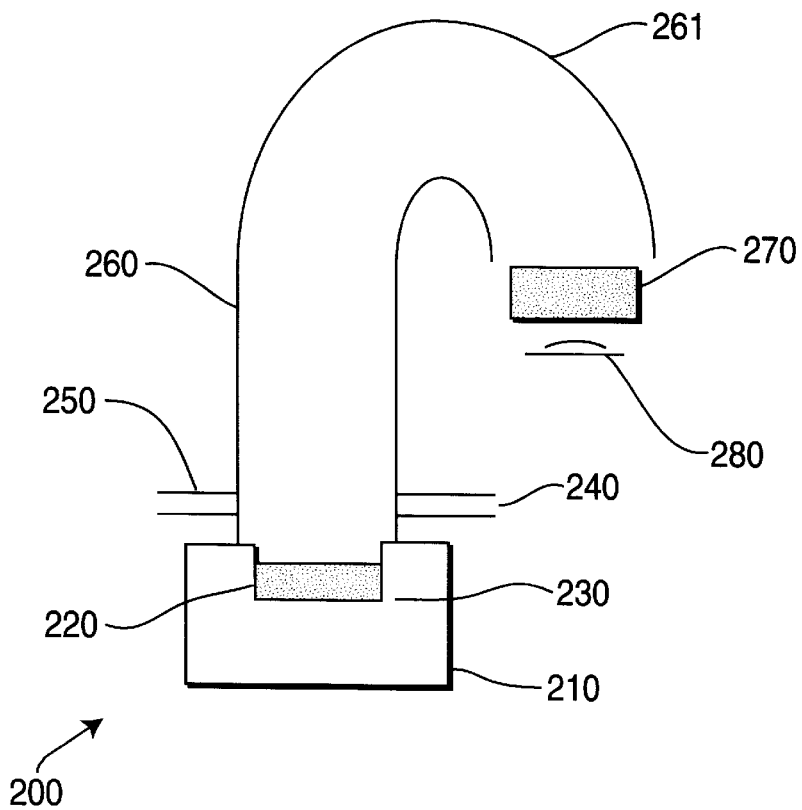
FIG. 2 displays a schematic diagram of fogging apparatus constructed to bind electrostatically deposited powders to membranes.

FIG. 2 shows a schematic diagram of a fogging apparatus 200 constructed to bind electrostatically deposited powders to membranes. The illustrated device comprises a liquid polymer solution 220 placed in a vessel 210 (for example, a "TEFLON" block) defining a cavity lined with an ultrasonic membrane 230. Air and liquid can enter the fogging apparatus 200 through a air inlet 250 and a liquid inlet 240. The fogging apparatus 200 was a curved glass tube 260 with an elbow 261, sealed to the "TEFLON" block 210. Ultrasonic agitation of the polymer solution 220 generates a chemical fog 270 that exits the fogging apparatus 200 and coats the deposited powder on the membrane 280.

In some embodiments, the substrate can be a membrane made, for example, from nitrocellulose or acetate. The substrate can be charged or neutral overall, and may have regions of charge aggregation or localized acid or base sites. In one embodiment of the invention, an adhered substrate layer can serve as the substrate surface for subsequent depositions. Thus, a device comprising layers of deposited particles segregated by film-forming polymer layers of variable composition can be made by the inventive method (FIG. 1).

FIG. 1 shows cross sections of various deposition configurations 100. Particles associated with a first chemical component 120 can be electrostatically deposited on a substrate surface 110. Deposition can be performed to make one continuous layer or in discrete spatially defined areas. A second and subsequent depositions can be performed with particles with a second chemical component 121, a third chemical component 122, or a fourth chemical component 123, or more components. Particles can also have multiple layers of mixtures of chemical components associated with their surfaces. After deposition, a first film-forming polymer layer 130 can be deposited to secure the deposited layer. In some embodiments, additional layers of particles associated, for example, with a third 122 or a fourth 123 chemical component can be added atop the first film-forming polymer layer. The deposition configuration of FIG. 1A can be formed by coating the substrate surface 110 with particles associated with a first chemical component 110 until a first monolayer of coverage is formed, followed by a second deposition with particles associated with a second chemical component 110 until a second monolayer of coverage is attained. The deposition configuration of FIG. 1A can be formed by: (i) coating the substrate surface 110 with particles associated with a first chemical component 120 with less than a monolayer coverage and in a spatially resolved manner, (ii) followed by a second deposition with particles associated with a second chemical component 121 also at sub-monolayer coverage levels and in a spatially defined manner, (iii) followed by a third deposition similar to the first deposition, (iv) followed by a fourth deposition similar to the second one, (v) followed by depositing a film-forming polymer layer 130 to secure the deposited layers. The configuration of FIG. 1B can allow for the mixing of the particles associated with the first chemical component 120 and second 121 chemical components. The configuration of FIG. 1C can be formed by performing a series of depositions similar to those for FIG. 1B, comprising a first and second deposition as in FIG. 1B above, but depositing a first film-forming polymer prior to subsequent deposition of particles associated with a third 122 and a fourth 123 chemical component. The third and fourth depositions are spatially resolved depositions, which can be submonolayer depositions. Finally, a second film-forming polymer layer 131 is applied.

Determining Bacterial Susceptibility

Biochemical assays for clinical specimen can require several manipulations. Initially, a sample processing step is required that entails application of the clinical sample onto a consumable device. The sample is processed or manipulated to allow for tissue or cellular lysis followed by extraction and purification of the analyte material. The analyte material is then tested by a variety of approaches that can include biochemical, enzymological, immunological or genetic technologies.

Several automated systems accomplish these tasks by performing multiple pipettings on board an instrument. A limitation of this approach is the potential for carry over contamination. Additional limitations include: sample tracking, the requirement for many disposables and dedicated instrument space for storage as well as performance of the assays. From a reagent perspective, biochemical and molecular biological reactions frequently require the addition of multiple reagents to facilitate a reaction. These reagents can be added at the start of the process or at defined times in the process. Addition of reagents at the onset can compromise the activity of a subset of the components. This compromise can be attributed to chemical incompatibilities or physical conditions that are not optimized for individual components.

Using methods of the present invention, processes generally performed as discrete independent steps are integrated into a single disposable unit. Separation of biological fluids is accomplished with membranes designed to fractionate bodily tissues. Using membranes, blood can be separated efficiently into serum and plasma components. Detection reagents, including dyes and enzymes are immobilized onto substrates using electrostatic interactions. This method can be applied to the addition of multiple layers of reagents. Reagents that are required early in the process are deposited adjacent to the sample processing membrane. Reagents that are required late in the reaction are deposited in a manner that they are physically segregated and sequestered from other reagent components. The composition of the material that segregates the reagent components can vary and allow for reagents to be released at a defined time in the process.

In a preferred embodiment, the method produces a substrate/particle device with a multilayered structure, with each layer allowing for a discrete function. The method of the invention also provides for fabricating a cell growth supporting substrate with spatially-resolved regions with associated bioactive agents, such as nutrients or antimicrobial components. Accordingly, the inventive method can comprise the association of bioactive agents with cell growth supporting substrate or a separate substrate that is incorporated into the cell growth supporting substrate.

Multi-functional Assay Structures

Bacterial drug resistance is evolving at an increasing rate in essentially every kind of bacterium that causes infection. Resistant microbes tend to appear where an antibiotic is used frequently. Several mechanisms account for drug resistance. As bacteria reproduce, mutations occur that allow for their ability to survive the drug. Additionally, bacteria can transfer their genetic instructions for avoiding an antibiotic to other bacterial species. To fight drug-resistant bacteria, overuse of antibiotics needs to be controlled. Successful determination of the requirement for an antibiotic and appropriate dosage necessitates strong surveillance systems.

In one embodiment of the present invention, antibiotics are attached onto a solid support using electrostatic mechanisms. Deposition of antibiotics onto a substrate using electrostatic interactions allows these drugs to be deposited in accurate and precise quantities. In addition to the ability to control the amount of material deposited, the process also allows for the precise positioning of the antibiotics on the surface of the substrate. In one approach, a charge is patterned on the surface of a substrate. Antibiotics that are charged with a complementary charge can be deposited onto the surface of the substrate.

In a preferred embodiment, a paper strip impregnated with several antibiotics of varying concentrations is placed onto the surface of a petri plate that has been streaked for culture growth. Visualization of the plate subsequent to incubation results in determining (a)whether a bacterial infection is present, (b) which antibiotics are effective for the particular strain, and (c) what is the appropriate concentration for the antibiotic.

Applications for this technology include screening for streptococci infections in the throat, wound infections with staphylococci, hospital-acquired infections with enterococci, pneumonae and meningitis infections (e.g., *Streptococcus pneumoniae* and *Hemophilus influenzae*), and community acquired infections caused by *E. coli*.

In another embodiment, the invention has application to the discovery and screening of new candidate antibiotics as well as antibiotic-resistant disablers. In one embodiment, a barcode system is affixed to various screening substrates made by the inventor to identify the screened compositions.

Devices or methods that can be used with various aspects of the present invention include, for example, the methods for use of transporter chucks, acoustic bead dispensers and other particle-manipulating devices set forth in Sun, "Chucks and Methods for Positioning Multiple Objects on a Substrate," U.S. Pat. No. 5,788,814, issued Aug. 4, 1998; Sun et al., "Electrostatic Chucks," U.S. Pat. No. 5,858,099, issued Jan. 12, 1999; Pletcher et al., "Apparatus for Electrostatically Depositing a Medicament Powder Upon Predefined Regions of a Substrate," U.S. Pat. No. 5,714,007, issued Feb. 3, 1998; Sun et al., "Method of making pharmaceutical using electrostatic chuck," U.S. Pat. No. 5,846,595, issued Dec. 8, 1998; Sun et al., "Acoustic Dispenser," U.S. Pat. No. 5,753,302, filed May 19, 1998; Sun, "Bead Transporter Chucks Using Repulsive Field Guidance," U.S. Pat. No. 6,096,368; Sun, "Bead manipulating Chucks with Bead Size Selector," , U.S. Pat. No. 5,988,432; Sun, "Focused Acoustic Bead Charger/Dispenser for Bead Manipulating Chucks," U.S. Pat. No. 6,168,666; Sun et al., "AC Waveforms Biasing For Bead Manipulating Chucks," U.S. Pat. No. 6,149,774; Sun et al, "Apparatus for Clamping a Planar Substrate," Ser. No. 09/095,321, filed Jun. 10, 1998.; Poliniak et al., "Dry Powder Deposition Apparatus," U.S. Pat. No. 6,063,194; and "Pharmaceutical Product and Method of Making," Ser. No. 09/095,616, filed Jun. 10, 1998. Moreover, Sun et al., "Device For The Dispersal And Charging Of Fluidized Powder," filed Oct. 14, 1999 (Attny. Docket DEL 13100) and Sun et al., "Electrostatic Sensing Chuck Using Area Matched Electrodes," filed Oct. 14, 1999 describes various apparatuses and methods for charging, sizing and manipulating particles. Further information on electrostatic deposition for making test strips and the like is found in Loewy et al., "Deposited Reagents for Chemical Processes," U.S. Pat. No. 6,095,753, and Loewy et al., "Solid Support With Attached Molecules," U.S. Pat. No. 6,004,752.

Definitions

The following terms shall have, for the purposes of this application, the respective meaning set forth below. bioactive agent. A bioactive agent is a substance such as a chemical that can act on a cell, virus, tissue, organ or organism, including but not limited to insecticides or drugs (i.e., pharmaceuticals) to create a change in the functioning of the cell, virus, organ or organism. Preferably, the organism is a mammal, more preferably a human. In preferred embodiments of the invention, methods of identifying bioactive agents of the invention are applied to organic molecules having molecular weight of about 1500 or less. Particles: Particles are, for the purposes of this application, aggregates of molecules, typically of at least about 3 nm average diameter, such at least about 500 nm or 800 nm average diameter, and are preferably from about 100 nm to about 5 mm, for example, about 100 nm to about 500 $\mu$m. Particles are, for example, particles of a micronized powder, or polymer structure that can be referred to as "beads." Beads can be coated, have adsorbed molecules, have entrapped molecules, or otherwise carry other substances.

The following examples further illustrate the present invention, but of course, should not be construed as in any way limiting its scope.

EXAMPLE 1

HIV Test Membrane

Peptides were electrostatically deposited onto a nitrocellulose membrane (Schleicher and Schuell) for use in an antigen/antibody type of assay. Small amounts of synthetic peptides were coated onto beads and the beads were subsequently mixed with an inert carrier. 0.19 $\mu$m latex particles (Fluorescent Nile Red latex, Cortex), or beads, were coated with streptavidin (Boeringer-Mannheim Corp.) using a carbodiimide reaction. After two hours of incubation in the streptavidin conjugation reaction, the particles were reacted with biotinylated synthetic peptide (corresponding to a segment of HIV- 1) overnight. The particles were washed and centrifuged and the wet pellet was mixed with d-lactose monohydrate and mixed thoroughly using a mortar and pestle. At this point, the mixture was in a fine powder form. Particle size measurements were conducted using an API Aerosizer-LD instrument (TSI Incorporated, Amherst, MA). Particle size reduction was found to be necessary, based on the performance and design of the particular deposition engine employed. Particle size reduction was accomplished by sieving the powder mixture through a 500 mesh screen. Particles of approximately 25 μm or less in size were produced. The deposition was performed using a prototype miniaturized dispenser described in Sun et al., U.S. patent application entitled "Device for the dispersal and charging of fluidized powder" filed Oct. 14, 1999 (Attny. Docket DEL 13100), wherein powder charging occurs by induction charging. The patterning of charge on the membrane by the electrostatic chuck was accomplished by the controlled field deposition process. Both the dispenser and the chuck were housed in a plastic containment box so that the humidity could be maintained at 30–35% relative humidity during the deposition. The size of the deposition are was approximately 5 mm in diameter. Deposition times were usually less than 10 seconds. The deposits could be seen by visual inspection. Additionally, photomicrographs were taken using a Leitz fluorescence microscope of the deposition of biotinylated synthetic peptide attached onto fluorescent beads. Assessment of the deposition process was facilitated by visualization of the microparticles using fluorescence microscopy.

The bead-based powder deposited on the membrane was loosely bound. To secure the powder so that the membrane could be handled or transported without the loss or displacement of powder, the powder deposit was lightly coated with a film-forming polymer to adhere the deposition to the membrane. To this end, an aqueous solution consisting of approximately 1% PVP (Sigma, St. Louis), 1% PEG 4500 (Sigma) and 0.2% polyethylenesorbitan monolaurate, sold under the trademark "TWEEN 20" (Sigma) was prepared and placed in an apparatus constructed for the purpose of producing a gentle fog of polymer material that, after landing on the deposited powder, acts to prevent the removal of the powder from the membrane. Samples were fogged for approximately 2 minutes or less and then were allowed to dry in room air. This procedure resulted in the deposited powder being well bound to the membrane.

The dry deposited synthetic HIV peptides coated on beads onto membranes were assayed with HIV positive clinical samples (done at AccuDx, San Diego, CA). All positive samples were clearly positive. Negative controls verified the result. The reagents remained fixed on the membranes during handling and transport. In addition, the peptide coated beads remained bound on the membranes when the assay was performed with fluid clinical specimens. The electrostatic deposition process apparently did not harm or degrade the peptides.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of fabricating a substrate having on a surface thereof two or more spatially-resolved regions, each with a defined amount or concentration of one of one or more chemical components, the method comprising:

(a) associating a chemical component with first particles of 1 μm to 500 μm diameter;

(b) electrostatically depositing the first particles on two or more appropriate said regions.

2. The method of claim 1, further comprising:

(c) associating a second chemical component with particles of 1 μm to 500 μm diameter to obtain second particles; and (d) after step (b), electrostatically depositing the second particles on two or more appropriate said regions, including at least one said region on which first particles were deposited.

3. The method of claim 1, wherein the chemical component comprises 20% w/w or less of the particles.

4. The method of claim 1, wherein the chemical component comprises 10% w/w or less of the particles.

5. The method of claim 1, wherein the chemical component comprises 5% w/w or less of the particles.

6. The method of claim 1, wherein the particles are polymeric particles or polymeric particles aggregated with carrier.

7. The method of claim 1, wherein the particles are polymeric particles of 0.1 μm to 5 μm diameter aggregated with carrier.

8. The method of claim 1, wherein the particles are polymeric particles of 0.1 μm to 1 μm diameter aggregated with carrier.

9. The method of claim 1, wherein the particles are latex or latex aggregated with carrier.

10. The method of claim 1, further comprising:

(e) associating the chemical component with preliminary particles, and the preliminary particles are aggregated with other solid components to form the first particles of 1 μm to 500 μm diameter.

11. The method of claim 1 wherein the chemical component is a peptide or protein.

12. The method of claim 1 wherein the chemical component is a nucleic acid.

13. The method of claim 1 wherein the chemical component is a nucleic acid-intercalating dye.

14. The method of claim 1, wherein the associating comprises covalently attaching.

15. The method of claim 1, wherein the associating comprises binding with an association constant of at least $10^{12}$ M-1.

16. The method of claim 1, further comprising:

(f) coating the regions with deposited first particles with a polymer composition adapted to secure the first particles to the surface.

17. A method of fabricating a cell growth supporting substrate with spatially-resolved regions with associated bioactive agents, the method comprising:

(a) associating a chemical component with first particles of 1 μm to 500 μm diameter;

(b) creating charge on the first particles; and (c) attracting the charge and thereby the first particles onto two or more appropriate said regions of a cell growth supporting substrate or a separate substrate that is incorporated into the cell growth supporting substrate.

18. The method of claim 17, wherein step (c) comprises depositing the first particles regions of a separate substrate, and the method further comprises:

(d) incorporating the separate substrate into the cell growth supporting substrate.

19. The method of claim 17, wherein the chemical component is a nutrient.

20. The method of claim 17, wherein the chemical component is an antimicrobial agent.

* * * * *

UNITED STATES PATENT AND TRADEMARK OFFICE
CERTIFICATE OF CORRECTION

| | |
|---|---|
| PATENT NO. | : 6,326,149 B1 |
| DATED | : December 4, 2001 |
| INVENTOR(S) | : Zvi Gerald Loewy, William Chiang, Hoi Cheong Sun and Bryan Lloyd Bentz |

It is certified that error appears in the above-identified patent and that said Letters Patent is hereby corrected as shown below:

Title page,
Item [75], Inventors: correct "Zyi Gerald Loewy" to read -- Zvi Gerald Loewy --.

Signed and Sealed this

Twenty-third Day of April, 2002

Attest:

Attesting Officer

JAMES E. ROGAN
Director of the United States Patent and Trademark Office